United States Patent [19]

Elango

[11] Patent Number: 5,179,229
[45] Date of Patent: Jan. 12, 1993

[54] PREPARATION OF 2,2-DIORGANO-3-ARYLPROPIONIC ACIDS AND ESTERS THEREOF

[75] Inventor: Varadaraj Elango, Corpus Christi, Tex.

[73] Assignee: Hoechst Celanese Corporation, Somerville, N.J.

[21] Appl. No.: 873,471

[22] Filed: Apr. 24, 1992

[51] Int. Cl.$^5$ .............................................. C07C 51/10
[52] U.S. Cl. .................................... 562/406; 560/105; 560/55; 560/51; 560/21; 560/9; 558/406
[58] Field of Search ......................... 562/406; 560/105

[56] References Cited

U.S. PATENT DOCUMENTS

| | | | |
|---|---|---|---|
| 4,166,131 | 8/1979 | Payne | 424/317 |
| 4,694,100 | 9/1987 | Shimizu | 560/105 |
| 4,981,995 | 1/1991 | Elango | 562/406 |
| 5,012,007 | 4/1991 | Elango | 508/311 |

FOREIGN PATENT DOCUMENTS

| | | |
|---|---|---|
| 284310 | 9/1988 | European Pat. Off. . |
| 55-27147 | 2/1980 | Japan . |
| 2242641 | 10/1987 | Japan . |
| 2242642 | 10/1987 | Japan . |
| 2263140 | 11/1987 | Japan . |

OTHER PUBLICATIONS

David E. Nichols, et al., "Effects of Certain Hallucinogenic Amphetamine Analogues on the Release of [$^3$H]Serotonin from Rat Brain Synaptosomes", *J. Medicinal Chemistry*, 25, 530–535 (1982).

Percy Warrick, Jr., et al., "The Migration Aptitude of Benzyl vs. in Methyl Carbonium Ion Reactions of the 2,2-Dimethyl-3-phenyl-1-propyl System"*J. Am. Chem. Soc.*, 4095–4100 (Nov. 5, 1962).

Boyd E. Hudson, Jr., et al., "Condensations. XIII. The Alkylation of Ethyl Isobutyrate and of Certain other Esters by Means of Sodium Triphenylmethyl and Alkyl Halides", *J. Am. Chem. Soc.*, 2457–2459 (Sep. 1940).

*Primary Examiner*—Paul J. Killos
*Attorney, Agent, or Firm*—James J. Mullen; Donald R. Cassady; J. Rosenstock

[57] ABSTRACT

A process for the preparation of 2,2-diorgano-3-arylpropionic acids is disclosed by the carbonylation of corresponding 2,2-diorgano-1-aryl ethanol in the presence of a Lewis acid catalyst. Furthermore, a process for the production of 2,2-diorgano-3-arylpropionic esters is disclosed by reacting a corresponding 2,2-diorgano-1-aryl ethanol with carbon monoxide and an alcohol in the presence of a Lewis acid catalyst.

20 Claims, No Drawings

PREPARATION OF 2,2-DIORGANO-3-ARYLPROPIONIC ACIDS AND ESTERS THEREOF

TECHNICAL FIELD OF THE INVENTION

The present invention relates to the field of 2,2-diorgano-3-arylpropionic acids and esters thereof and, more particularly, to a method of preparing such acids and esters. Still more particularly, the present invention relates to the preparation of 2,2-diorgano-3-arylpropionic acids and esters thereof by the carbonylation of corresponding 2,2-diorgano-1-arylethanol in the presence of a Lewis acid catalyst.

BACKGROUND OF THE INVENTION

The compounds 2,2-diorgano-3-arylpropionic acids are known compounds which are used as intermediates in the production of pharmaceuticals and herbicides. For example, 2,2-dialkyl-3-phenylpropionic acids are intermediates for the production of 2,2-dialkyl-1-indanones. An example of such preparation includes the preparation of 2,2-dimethyl-1-indanone by treating 2,2-dimethyl-3-phenylpropionic acid with a Lewis acid such as anhydrous hydrogen fluoride. 2,2-Dialkyl-1-indanones such as 2,2-dimethyl-1-indanone and 2,2-diethyl-1-indanone are valuable intermediates in the pharmaceutical industry. For example, 2,2-dimethyl-1-indanone is used in the synthesis of antiallergic agent 4-(6'-chloro-2',2'-dimethylinden-1'-ylidene)-1-methylpiperidine, the anti-inflammatory and anti-arthritic indane-5-acetic acid derivatives disclosed in U.S. Pat No. 4,166,131, and other bioactive compounds such as coumarins. Furthermore, the 2,2-diorgano-3-arylpropionic acids produced in accordance with the present invention, for example, 2,2-dialkyl-3-phenylpropionic acids and, more particularly, 2,2-dimethyl-3-phenylpropionic acids, are valuable intermediates for the production of antibiotics, cardiovascular agents, anticholesterimic agents and herbicides.

2,2-Diorgano-3-arylpropionic acids have been prepared in the past by several different methods. Nichols et al., *Effects of Certain Hallucinogenic Amphetamine Analogues on the Release of [3'] Serotonin from Rat Brain Synaptosomes*, J. Med. Chem., 25, 530–535 (1962) discloses the preparation of 2,2-dimethyl-3-(4-methoxyphenyl)propionic acid and 2,2-dimethyl-3-[3,4-(methylenedioxyl)phenyl]propionic acid.

Carbonylation of alcohols to form acids has been used in the past. For example, Japanese Kokai Patent No. SHO 55[1980]-27147, published on Feb. 27, 1980, discloses the preparation of 2-(4'-isobutyl-phenyl)propionic acid by reacting 2-(4'-isobutyl-phenyl)ethanol with carbon monoxide and water in the presence of hydrogen fluoride. In that process, like in other prior processes involving a Koch reaction, the carboxyl group forming the acid was bonded to the same carbon atom that the hydroxyl group of the reactant alcohol was bonded to prior to the carbonylation.

U.S. Pat. No. 4,981,995 discloses the preparation of 2-(4'-isobutylphenyl)propionic acid by carbonylating 1-(4'-isobutylphenyl)ethanol with carbon monoxide in an acidic aqueous medium using a palladium complex. A small amount of 3-(4'-isobutylphenyl)propionic acid is formed as a byproduct involving the bonding of the carboxyl group to a carbon which is not the same as the carbon that the hydroxyl group of the reactant alcohol is bonded to prior to the carbonylation. This shift of the carbonylation to a different carbon atom is attributed to the presence of the transition metal catalyst, i.e., the palladium complex.

U.S. Pat. No. 5,012,007 discloses the preparation of a propionic acid and, more particularly, 2,2,dimethyl-3-(4'-methoxyphenyl)propanoic acid by carbonylating 1,(4'-methoxyphenyl)-2-methyl-1-propanol in the presence of hydrogen fluoride at room temperature in a reactor pressurized to 450 psig with carbon monoxide. The reaction also produced a larger amount of 6-methoxy-2,2-dimethyl-1-indanone. In that patent, the reactant carbinols are characterized by the fact that at least one of the ring carbons which is in a position adjacent to the 1-position of the ring is bonded to a hydrogen. That together with the temperature of the reaction cause the cyclization of the reactant to form the indanone.

Other than the specific and limited disclosure of U.S. Pat. No. 5,012,007, none of the above referenced or any other prior process disclose the preparation of 2,2-diorgano-3-arylpropionic acids from corresponding 2,2-diorgano-1-arylethanol by carbonylating such carbinols in the presence of a Lewis acid catalyst. The present invention discloses such process.

2,2-Diorgano-3-arylpropionic acid esters have been prepared in the past by reacting an aryl chloride with methyl isobutyrate in the presence of a base. Warrich et al., *The Migration Aptitude of Benzyl vs. Methyl in Carbonium Ion Reaction of the 2,2-dimethyl-3-phenyl-1-propyl System*, J. Am. Chem. Soc., 4095–4100 (1962) describes the reaction of benzyl chloride with methyl isobutyrate in the presence of a base such as sodium hydride to form 2,2-dimethyl-3-phenylpropionic acid methyl ester. U.S. Pat. No. 4,166,131 discloses the preparation of 2,2-dimethyl-3-(4'-chlorophenyl)propionate by reacting 4-chlorobenzyl chloride with methyl isobutyrate in the presence of a base such as sodium hydride. None of these processes discloses the preparation of 2,2-diorgano-3-arylpropionic acid esters from corresponding 2,2-diorgano-1-arylethanol by the carboalkoxylation in the presence of a Lewis acid catalyst.

These and other objects and advantages of the present invention will become apparent from the following description.

SUMMARY OF THE INVENTION 2,2-Diorgano-3-arylpropionic acids are prepared by carbonylating a corresponding 2,2-diorgano-1-arylethanol in the presence of a Lewis acid catalyst such as hydrogen fluoride, boron fluoride or aluminum chloride. The reaction is preferably carried out in the presence of water. In an alternative embodiment of the invention, a 2,2-diorgano-3-arylpropionic acid ester is prepared by reacting a corresponding 2,2-diorgano-1-arylethanol with carbon monoxide and an alcohol in the presence of a Lewis acid catalyst such as hydrogen fluoride, boron fluoride or aluminum chloride. The reaction is carried out at a carbon monoxide partial pressure in the range of about 50 to 2,000 psig and preferably in the range of about 100 to about 1000 psig.

DETAILED DESCRIPTION OF THE INVENTION

According to the present invention, a process for the production of 2,2-diorgano-3-arylpropionic acids is disclosed by the carbonylation of corresponding 2,2-diorgano-1-arylethanol in the presence of a Lewis acid catalyst. The 2,2-diorgano-3-arylpropionic acids produced in accordance with the present invention are of the formula (Formula 1):

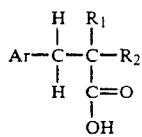

The corresponding reactant 2,2-diorgano-1-arylethanol are of the formula (Formula 2):

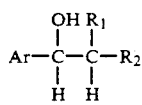

In Formulas 1 and 2, $R_1$ and $R_2$ are independently an alkyl group containing 1 to 18 and, preferably, 1 to 4 carbon atoms, an unsubstituted aryl group or a substituted aryl group wherein at least one ring carbon is bonded to an alkyl group, an alkoxy group, a halogen or a hydroxy group. The unsubstituted or substituted aryl groups are preferably phenyl groups. Furthermore, in Formulas 1 and 2, Ar is an unsubstituted or a substituted aryl group, preferably a phenyl group. When Ar is a substituted aryl group, it is independently substituted in one or more substitutable positions with the substituents being independently hydrogen, a halogen, nitrogen, a hydroxy group, an alkoxy group, an aryloxy group, an aryl group, an acyl group, a cyano group, a thioalkoxy group or an alkyl group containing 1 to 18 and, preferably, 1 to 4 carbon atoms. When the substituents are an aryl group or an acyl group, those groups are preferably a phenyl group or an acetyl group, respectively. It should be understood that, unless stated otherwise, the above definition of $R_1$, $R_2$, and Ar shall be applicable hereinafter.

In accordance with the present invention, the carbonylation reaction to prepare the propionic acids of Formula 1 is carried out stoichiometrically as follows (Reaction 1):

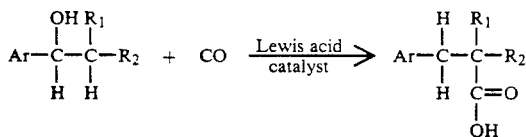

An example of a product prepared in accordance with Reaction 1 is 2,2-dimethyl-3-(4'-chlorophenyl)propionic acid which is produced by carbonylating 1-(4'-chlorophenyl)-2-methyl-1-propanol. Another example of such product is 2,2-dimethyl-3-(4'-methoxyphenyl)propionic acid produced by carbonylating 1-(4'-methoxyphenyl)-2-methyl-1-propanol.

Although it is not necessary to carry out the reaction of the present invention, it is preferred, however, that water be added in the reaction mass to convert substantially all of the compound of Formula 2 to the compound of Formula 1.

In an alternative embodiment of the present invention, a 2,2-diorgano-3-arylpropionic acid ester is prepared by carbonylating and esterifying an 2,2-diorgano-1-aryl ethanol of Formula 2 in the presence of a Lewis acid catalyst. The ester is of the formula (Formula 3):

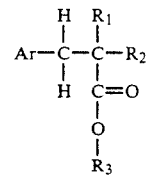

wherein $R_1$, $R_2$ and Ar are as defined above and $R_3$ is an organic group, preferably an alkyl group containing one to 18 carbon atoms, and, most preferably, an alkyl group containing one to four carbon atoms.

The reaction for the preparation of the ester is represented stoichiometrically as follows (Reaction 2):

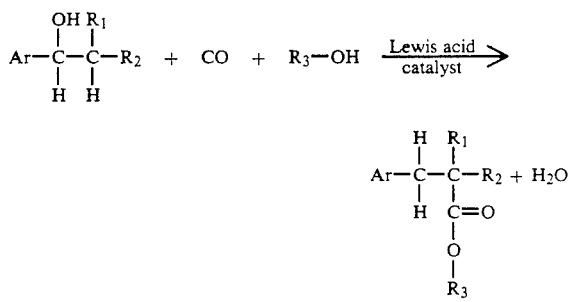

Any Lewis acid catalyst or mixtures thereof may be used to carry out the reactions of the present invention. The most preferred catalyst, however, is hydrogen fluoride (HF) and preferred catalysts are aluminum chloride ($AlCl_3$) and boron fluoride ($BF_3$) or a mixture thereof. The amount of Lewis catalyst may range from 0.1 mole to 200 mole per mole of reactant. An excess amount of catalyst, however, in the range of about one (1) to about one hundred (100) moles of catalyst per mole of reactant is preferred.

Although one mole of carbon monoxide is required to carbonylate one mole of reactant to produce the product in accordance with the present invention, it is preferred that an excess amount of carbon monoxide be used in the reaction. Accordingly, the amount of carbon monoxide is in the range of about one (1) to about five hundred (500) moles of carbon monoxide per mole of reactant. This is accomplished by maintaining the carbon monoxide pressure in the reactor at about 50 to about 2000 psig and, preferably, at about 100 to about 1000 psig.

In carrying out Reactions 1 or 2, the liquid feed carbinol reactant, the gas carbon monoxide and the catalyst are charged to a corrosion-resistant reactor. Furthermore, in carrying out Reaction 2, the alcohol of formula $R_3$—OH is also added. As stated above, the pressure of the gas carbon monoxide is maintained at about 50 to about 2000 psig and, preferably, at about 100 to about 1000 psig. The catalyst may be fed in as a gas, a liquid or a solid by techniques well known to those skilled in the art. If a catalyst having a low boiling point is used such as HF or $BF_3$ it is preferred that the catalyst be fed at a low temperature to avoid safety problems. In that case, prior to feeding the catalyst to the reactor, the reactor is cooled to a temperature which is below the boiling point of the catalyst. In the case of hydrogen fluoride, for example, the reactor is cooled to as low as −50° C. and preferably to about −30° C. Then, the reaction mixture is heated to the desired reaction temperature.

Although the reaction proceeds in accordance with the present invention at temperatures lower than 20° to 25° C., it is preferred that the reaction be carried out at a temperature in the range of about 20° C. to about 125° C. and, most preferably, in the range of about 20° C. to about 60° C., if the catalyst is hydrogen fluoride. In the case, however, wherein Ar is an aryl group which is not substituted in either of the positions which are adjacent to the carbinol carbon atom or in the case wherein Ar is a substituted aryl group wherein substituents are electron donating group such as hydroxy or alkoxy, the reaction temperature must not exceed 30° C. to prevent the cyclization of the 2,2-diorgano-3-arylpropionic acid to an indanone compound.

Although it is not necessary to carry out Reactions 1 and 2, an inert gas such as nitrogen may be employed to cause sufficient amount of catalyst such as hydrogen fluoride to be in contact with the reaction liquid. Furthermore, although it is not necessary, Reactions 1 and 2 may be carried out in the presence of a solvent. Preferably, an inert solvent such as, for example, a straight chain alkane containing about 5 to 12 carbon atoms may be employed. Other solvents include water, $C_1$–$C_4$ alcohols, chlorinated hydrocarbons, aromatic hydrocarbons, ethers, esters and aprotic solvents such as dimethylsulfoxide. If a solvent is used, it may be present at a weight ratio of solvent to feed carbinol of about 1 to 20 and, preferably, about 2 to 10.

Depending on the degree of heating and the nature of the reactants, the reactions of the present invention are carried out for a period of about 0.1 to about 24 hours and, preferably, about 1 to about 6 hours.

The reactant carbinols used in accordance with the present invention are produced by several well known methods. An example of such method is the reduction of the appropriate ketones with hydrogen and a catalyst or hydride reagents like lithium aluminum hydride and sodium borohydride. The ketones are prepared by the acylation of an aryl compound with ($\alpha,\alpha$-diorgano)acetic acid, its anhydride, acid fluoride or acid chloride using a Lewis acid catalyst.

At the end of the reaction, the reaction mass contains the propionic acids or the esters thereof prepared in accordance with the present invention and other by products. The desired product is obtained by separating it from the reaction mass by well known separation techniques such as solvent extraction, distillation, crystallization and chromatography.

The following examples further illustrate the invention, but are not to be construed as limitations on the scope of the invention contemplated herein.

EXAMPLE 1

Preparation of 4-chloroisobutyrophenone

Isobutyryl chloride (216 grams, 2.02 moles) was added over 90 minutes to a suspension of anhydrous aluminum chloride (268 grams, 2.0 moles) in chlorobenzene (1000 ml, 9.84 moles). The reaction mass was stirred at room temperature for about 23 hours. Then, the reaction mass was poured into crushed ice (1600 grams). The mixture was extracted with methylene chloride (3 times with 400 ml of methylene chloride each time). A combined organic extract was washed with water (400 ml), dried with anhydrous $MgSO_4$, filtered and concentrated to give crude product. The crude product was distilled under vacuum (boiling point 80° C. at 0.25 mm Hg) to yield 4-chloroisobutyrophenone (365 grams corresponding to 75% yield).

EXAMPLE 2

Preparation of 1-(4'-Chlorophenyl)-2-methyl-1-propanol

A solution of 4-chloroisobutyrophenone (50 grams, 0.27 moles) in ethanol (150 ml) was prepared. Sodium borohydride (5.67 grams, 0.15 moles) was added in portions over a two hour period to that solution under nitrogen. The reaction mass was stirred at room temperature for about two hours. Ethanol was then removed under reduced pressure. The reaction mass was added to water (200 ml) and acidified with 10% hydrochloric acid (50 ml). The mixture was extracted with methylene chloride (2 times with 250 ml of methylene chloride each time). The combined organic extract was collected, dried with anhydrous magnesium sulfate and concentrated to yield 1-(4'-chlorophenyl)-2-methyl-1-propanol (51 grams corresponding to 98% yield). The product was purified by vacuum distillation (boiling point 90°–91° C. at 0.5 mmHg).

EXAMPLE 3

Carbonylation of 1-(4'-chlorophenyl)-2-methyl-1-propanol 1-(4'-Chlorophenyl)-2-methyl-1-propanol (9.6 grams, 0.05 moles), water (3.8 grams, 0.21 moles) and hexane (32 grams) were charged into a 300 cubic centimeter Hastelloy C autoclave. The autoclave was purged twice with nitrogen, evacuated to 100 mm Hg, and cooled to −30° C. Hydrogen fluoride (75.0 grams, 3.25 moles) was then added and the reactor was pressurized to 600 psig with carbon monoxide. The reaction mass was stirred for about one hour at room temperature. The hydrogen fluoride was vented and the contents were removed and poured onto crushed ice. A solution of 45% potassium hydroxide was added to the mixture until the pH of the mixture was adjusted to 6.0–6.5. The mixture was then extracted with ethyl acetate (3 times with 150 ml of ethyl acetate each time). The combined organic extract was dried with anhydrous magnesium sulfate, filtered and concentrated to yield the crude product (9.8 grams). The crude product was analyzed by GLC. The analysis showed that the crude product contained 1-(4'-chlorophenyl)-2-methyl-1-propene (3.9%) and 2,2-dimethyl-3-(4'-chlorophenyl)propanoic acid 82%. The crude product was then crystallized using a mixture containing equal amounts of ethyl acetate and hexane to yield pure 2,2-dimethyl-3-(4'-chlorophenyl)propanoic acid (8.5 grams corresponding to 80% yield).

EXAMPLE 4

Preparation of 4-Methoxyisobutyrophenone

Sodium hydroxide (6.9 grams, 0.17 moles) was dissolved in water (75 ml). 4-Hydroxyisobutyrophenone (25.1 grams, 0.15 moles) was added to the solution. Then, dimethyl sulfate (22.6, 0.18 moles) and tetrabutylammonium iodide (0.55 grams, 1.5 millimoles) were added and the reaction mass was refluxed for about three hours. The mixture was then cooled to room temperature and then extracted with methylene chloride (3 times with 150 ml of methylene chloride each time). The combined organic extract was washed with water (100 ml), dried with anhydrous magnesium sulfate, filtered and concentrated to yield 4-methoxyisobutyrophenone with 77.4% purity (23.2 grams corresponding to 65% yield). The crude product was purified by distillation.

EXAMPLE 5

Preparation of
1-(4'-Methoxyphenyl)-2-methyl-1-propanol

A solution of 4-methoxyisobutyrophenone (14.6 grams, 0.082 moles) in ethanol (150 ml) was prepared. Sodium borohydride (2.6 grams, 0.069 moles) was added to the solution in portions over a one hour period under nitrogen. The reaction mass was stirred at room temperature for about two hours. Ethanol was removed under reduced pressure. The reaction mass was added to water (200 ml) and acidified with 10% hydrochloric acid (50 ml). The mixture was then extracted with methylene chloride (3 times with 100 ml of methylene chloride each time). The combined organic extract was collected, dried with anhydrous magnesium sulfate and concentrated to yield 1-(4'-methoxyphenyl)-2-methyl-1-propanol having a purity of 90% (12.5 grams corresponding to 76% yield). The crude product was purified by vacuum distillation (boiling point 89°–91° C. at 0.5 mmHg).

EXAMPLE 6

Carbonylation of
1-(4'-Methoxyphenyl)-2-methyl-1-propanol 1-(4'-Methoxyphenyl)-2-methyl-1-propanol (5.75 grams, 0.032 moles), water (2.1 grams, 0.13 moles), and hexane (32 grams) were charged into a 300 cubic centimeter Hastelloy C autoclave. The autoclave was purged twice with nitrogen, evacuated to 100 mm Hg and cooled to −20° C. Hydrogen fluoride (75.0 grams, 3.25 moles) was added and the reactor was pressurized to 450 psig with carbon monoxide. The reaction mass was stirred for about one hour at 20° C. The hydrogen fluoride was vented. Then the contents were removed and poured onto crushed ice. A solution of 45% potassium hydroxide was added to the mixture until the pH was adjusted to 6.5–7.0. The mixture was then extracted with ethyl acetate (3 times with 150 ml of ethyl acetate each time). The combined organic extract was dried with anhydrous manganese sulfate, filtered and concentrated to yield the crude product (5.0 grams). The crude product was analyzed by GLC. The analysis showed that it contained 2,2-dimethyl-3-(4'-methoxyphenyl)-propanoic acid (16%), and other products.

EXAMPLE 7

Preparation of Ethyl
2,2-dimethyl-3-(4'-chlorophenyl)-propanoate 1-(4'-Chlorophenyl)-2-methyl-1-propanol (9.6 grams, 0.05 moles), ethanol (4.5 grams, 0.1 mole), and hexane (32 grams) are charged into a 300 cubic centimeter Hastelloy C autoclave. The autoclave is purged twice with nitrogen, evacuated to 100 mm Hg, and cooled to −30° C. Hydrogen fluoride (75 grams, 3.25 mole) is then added and the reactor is pressurized to 600 psig with carbon monoxide. The reaction mass is stirred for about an hour at room temperature. The hydrogen fluoride is vented and the contents are removed and poured onto crushed ice. A solution of 45% potassium hydroxide is added to the mixture until the pH of the mixture is adjusted to 6.0–6.5. The mixture is then extracted with ethyl acetate (3 times with 150 ml of ethyl acetate each time). The combined organic extract is dried with anhydrous magnesium sulfate, filtered, and concentrated to yield the crude product. The crude product is distilled under vacuum to give pure ethyl 2,2-dimethyl-3-(4'-chlorophenyl)propanoate.

While the invention is described with respect to specific embodiments, modifications thereof can be made by one skilled in the art without departing from the spirit of the invention. The details of said embodiments are not to be construed as limitations except to the extent indicated in the following claims.

What is claimed is:

1. A method of preparing a compound of the formula:

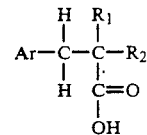

comprising the step of reacting a compound of the formula:

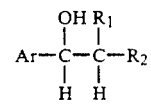

with carbon monoxide, in the presence of a Lewis acid catalyst, wherein $R_1$ and $R_2$ are independently an alkyl group containing one to 18 carbon atoms, an unsubstituted aryl group or a substituted aryl group wherein at least one ring carbon is bonded to an alkyl group, an alkoxy group, a halogen or a hydroxy group, and wherein Ar is an unsubstituted aryl radical or a substituted aryl radical substituted independently at one or more substitutable positions.

2. The method according to claim 1 wherein Ar is a substituted aryl radical and the substituents are independently hydrogen, a halogen, nitrogen, a hydroxy group, an alkoxy group, an aryloxy group, an aryl group, an acyl group, a cyano group, a thioalkoxy group or an alkyl group containing one to 18 carbon atoms.

3. The method according to claim 1 wherein Ar is a substituted or unsubstituted phenyl group.

4. The method according to claim 1, wherein the aryl groups are phenyl groups.

5. The method according to claim 1 wherein the alkyl group contains 1 to 4 carbon atoms.

6. The method according to claim 1 wherein $R_1$ and $R_2$ are methyl groups and Ar is a 4-chlorophenyl group.

7. The method according to claim 1 wherein $R_1$ and $R_2$ are methyl groups and Ar is a 4-methoxyphenyl group.

8. The method according to claim 1 further including the step of adding water.

9. The method according to claim 1 wherein the catalyst is hydrogen fluoride, aluminum chloride or boron fluoride.

10. The method according to claim 1 wherein the reacting step is carried out at a temperature in the range of about 20° C. to about 125° C.

11. A method of producing a compound of the formula:

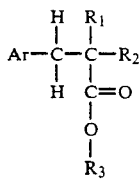

comprising the step of reacting a compound of the formula:

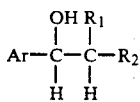

with carbon monoxide and an alcohol of the formula $R_3$—OH, in the presence of a Lewis acid catalyst, wherein $R_3$ is an organic group and $R_1$ and $R_2$ are independently an alkyl group containing one to 18 carbon atoms, an unsubstituted aryl group or a substituted aryl group wherein at least one ring carbon is bonded to an alkyl group, an alkoxy group, a halogen or a hydroxy group and wherein Ar is an unsubstituted aryl radical or a substituted aryl radical substituted independently at one or more substitutable positions.

12. The method according to claim 11 wherein Ar is a substituted aryl radical and the substituents are independently hydrogen, a halogen, nitrogen, a hydroxy group, an alkoxy group, an aryloxy group, an aryl group, an acyl group, a cyano group, a thioalkoxy group or an alkyl group containing one to 18 carbon atoms.

13. The method according to claim 11 wherein Ar is a substituted or unsubstituted phenyl group.

14. The method according to claim 11 wherein the aryl groups are phenyl groups.

15. The method according to claim 11 wherein the alkyl group contains 1 to 4 carbon atoms.

16. The method according to claim 11 wherein $R_1$ and $R_2$ are methyl groups and Ar is a 4-chlorophenyl group.

17. The method according to claim 11 wherein $R_1$ and $R_2$ are methyl groups and Ar is a 4-methoxyphenyl group.

18. The method according to claim 11 further including the step of adding water.

19. The method according to claim 11 wherein the catalyst is hydrogen fluoride, aluminum chloride or boron fluoride.

20. The method according to claim 11 wherein the reacting step is carried out at a temperature in the range of about 20° C. to about 125° C.

* * * * *